United States Patent [19]

Miyata et al.

[11] Patent Number: 5,679,844

[45] Date of Patent: *Oct. 21, 1997

[54] MANUFACTURING METHOD FOR PHOSPHONIC ACID DERIVATIVES

[75] Inventors: Hideo Miyata; Toru Sasaki; Kohei Morikawa, all of Kawasaki, Japan

[73] Assignee: Showa Denko K.K., Tokyo, Japan

[*] Notice: The term of this patent shall not extend beyond the expiration date of Pat. No. 5,453,537.

[21] Appl. No.: 605,056

[22] PCT Filed: Jul. 3, 1995

[86] PCT No.: PCT/JP95/01327

§ 371 Date: Mar. 1, 1996

§ 102(e) Date: Mar. 1, 1996

[87] PCT Pub. No.: WO96/01264

PCT Pub. Date: Jan. 18, 1996

[30] Foreign Application Priority Data

Jul. 1, 1994 [JP] Japan ................... 6-151004

[51] Int. Cl.$^6$ ........................ C07F 9/38
[52] U.S. Cl. ........................ 562/17
[58] Field of Search ................... 562/17

[56] References Cited

U.S. PATENT DOCUMENTS

| | | |
|---|---|---|
| 3,799,758 | 3/1974 | Franz . |
| 3,923,877 | 12/1975 | Barton .................... 260/502.5 |
| 3,977,860 | 8/1976 | Franz . |
| 4,221,583 | 9/1980 | Gaertner et al. .................... 71/86 |
| 4,415,503 | 11/1983 | Robbins . |
| 5,453,537 | 9/1995 | Morikawa et al. . |

FOREIGN PATENT DOCUMENTS

| | | |
|---|---|---|
| 49-93323 | 9/1974 | Japan . |
| 604840 | 2/1985 | Japan . |
| 4-279595 | 10/1992 | Japan .................... C07F 9/38 |
| 0 537 786 | 4/1993 | Japan . |

OTHER PUBLICATIONS

International Search Report Sep. 26, 1995.

*Primary Examiner*—Gary Geist
*Assistant Examiner*—Jean F. Vollano
*Attorney, Agent, or Firm*—Sughrue, Mion, Zinn, Macpeak & Seas, PLLC

[57] ABSTRACT

The present invention relates to a method of manufacturing N-phosphonomethylglycine and salts thereof, which can be biologically degraded, and have superior effectiveness against weeds and are useful as herbicides, by means of alkali hydrolysis of N-phosphonomethylglycinonitrile. In order to obtain high yields of the desired high purity, the amount of salt produced as a by-product is reduced by using the alkali so as to result in not less than 2 molecules and less than 3 molecules of the alkali for each molecule of N-phosphonomethylglycinonitrile when the alkali is monovalent, and not less than 1 molecule and less than 1.5 molecules of the alkali for each molecule of N-phosphonomethylglycinonitrile when the alkali is divalent.

10 Claims, No Drawings

1

MANUFACTURING METHOD FOR PHOSPHONIC ACID DERIVATIVES

TECHNICAL FIELD

The present invention relates to a manufacturing method for N-phosphonomethylglycine and salts thereof which are phosphonic acid derivatives and are useful as herbicides and starting materials and the like for herbicides.

BACKGROUND ART

N-phosphonomethylglycine and salts thereof, for example, glyphosate, sodium glyphosate, ammonium glyphosate, glyphosate-monodimethylamine, glyphosphate trimethylsulfonium salt (sulfosate), glyphosamine, and the like, can be biologically degraded, in addition, they are effective for use in small amounts as herbicide, and are either being used widely, or are having their effectiveness examined.

There are many known manufacturing methods for N-phosphonomethylglycine; there are methods which use N-phosphonomethylglycinonitrile as a starting material or intermediate, which can be converted into the desired N-phosphonomethylglycine by means of hydrolysis of the nitrile group of the N-phosphonomethylglycinonitrile.

Moreover, manufacturing methods for N-phosphonomethylglycinonitrile are described in, for example, Japanese Patent Application, Second Publication, No. Sho 60-4840; Japanese Patent Application, First Publication, No. Hei 4-279595; U.S. Pat. No. 4,221,583; etc.

With regard to the hydrolysis of N-phosphonomethylglycinonitrile, hydrolysis by means of sodium hydroxide is given as an example in U.S. Pat. No. 4,221,583.

In addition, Japanese. Patent Application, First Publication, No. Hei 4-279595 describes a reaction of aminomethylphosphonic acid and glycolonitrile, wherein not less than twice the number of moles of alkali metal hydroxide, compared with the aminomethylphosphonic acid, are added and reacted. Hydrolysis takes place by the addition of additional alkali metal hydroxide in amounts sufficient to neutralize the carboxylic acid generated as a result of the hydrolysis of the nitrile group of the obtained N-phosphonomethylglycinonitrile.

In the isolation of N-phosphonomethylglycine from the aqueous solution resulting from the alkali hydrolysis of N-phosphonomethylglycinonitrile, since a method of neutralization using acid takes place, a salt by-product is produced by the use of alkali metal hydroxide, and dealing with this salt by-product is expensive and laborious.

An object of the present application is to provide a manufacturing method for N-phosphonomethylglycine which brings about a reduction in the salt by-product which is produced by using alkali, such as alkali metal hydroxides or alkaline-earth metal hydroxides, and which is a major problem when manufacturing N-phosphonomethylglycine by means of alkali hydrolysis of N-phosphonomethylglycinonitrile; moreover, the present application aims to provide a manufacturing method for N-phosphonomethylglycine which is industrially advantageous, and achieves high purity and high yields.

DISCLOSURE OF THE INVENTION

The manufacturing method for the phosphonic acid derivatives of the present invention is a method in which N-phosphonomethylglycine and salts thereof are obtained by hydrolysis using alkali so as to result in not less than 2 molecules and less than 3 molecules of the alkali for each molecule of the N-phosphonomethylglycinonitrile when the alkali cation is monovalent, and using the alkali so as to result in not less than 1 molecule and less than 1.5 molecules of the alkali for each molecule of the N-phosphonomethylglycinonitrile when the alkali cation is divalent.

As the above-mentioned alkali, it is preferable to use alkali metal hydroxides or alkaline-earth metal hydroxides. When using alkali metal hydroxides, the alkali metal hydroxides so as to result in 2 molecules or more and less than 3 molecules, preferably 2.1 molecules or more and less than 2.7 molecules of the alkali metal hydroxides for each molecule of N-phosphonomethylglycinonitrile are used. In addition, when using alkaline-earth metal hydroxides, the alkaline-earth metal hydroxides so as to result in 1 molecule or more and less than 1.5 molecules, preferably 1.05 molecules or more and less than 1.35 molecules of the alkaline-earth metal hydroxides for each molecule of N-phosphonomethylglycinonitrile are used.

In addition, it is preferable that the hydrolysis reaction take place in a closed system.

Furthermore, this invention provides a method for obtaining N-phosphonomethylglycine and salts thereof by means of a first step in which aminomethyl phosphonic acid and glycolonitrile react in the presence of alkali so as to result in not less than 1.5 molecules and less than 2.5 molecules of the alkali for each molecule of the aminomethyl phosphonic acid when the alkali is monovalent, and not less than 0.75 molecules and less than 1.25 molecules of the alkali for each molecule of the aminomethyl phosphonic acid when the alkali is divalent; and a second step in which, without isolating said N-phosphonomethylglycinonitrile obtained in the first step, hydrolysis takes place using sufficient alkali to neutralize the carboxylic acid generated; wherein the total amount of alkali used in the first step and the second step results in not less than 2 molecules and less than 3 molecules for each molecule of the N-phosphonomethylglycinonitrile when the alkali is monovalent, and not less than 1 molecule and less than 1.5 molecules for each molecule of the N-phosphonomethylglycinonitrile when the alkali is divalent.

BEST MODE FOR CARRYING OUT THE INVENTION

The inventors accomplished the present invention as a result of repeated consideration of various methods of manufacturing N-phosphonomethylglycine by means of alkali hydrolysis of N-phosphonomethylglycinonitrile, and surprisingly discovered a way to obtain N-phosphonomethylglycine of high purity at a high yield by advancing hydrolysis by the addition of alkali metal hydroxide so as to result in less than 3 molecules of the alkali metal hydroxide for each molecule of N-phosphonomethylglycinonitrile, or by the addition of alkaline-earth metal hydroxides so as to result in less than 1.5 molecules of the alkaline-earth metal hydroxides for each molecule of N-phosphonomethylglycinonitrile.

The N-phosphonomethylglycinonitrile used in the present invention is not particularly limited, for example, N-phosphonomethylglycinonitrile obtained by means of the manufacturing methods described in Japanese Patent Application, Second Publication, No. Sho 60-4840; Japanese Patent Application, No. Hei 4-279595; U.S. Pat. No. 4,221,583; and the like can be used.

In addition, as the alkali used in the present invention, alkali metal hydroxides such as sodium hydroxide, and alkaline-earth metal hydroxides such as calciumhydroxide are preferable; however, other than these, alkalis which show alkaline properties in aqueous solutions such as ammonium hydroxide, sodium carbonate, ammonium carbonate, sodiumphosphate, sodium bicarbonate, and the like can be used.

As the alkali metal hydroxide used in the present invention, from an economical point of view as well, sodium hydroxide and potassium hydroxide are preferable. As alkaline-earth metal hydroxides, magnesium hydroxide, calcium hydroxide, and the like can be mentioned. In addition, it is possible to use alkali metal hydroxides and alkaline-earth metal hydroxides together to achieve the necessary quantities for addition mentioned above.

In the present invention, when the alkali cation is monovalent, hydrolysis is conducted using alkali so as to result in 2 molecules or more and less than 3 molecules of the alkali, and preferably 2.1 molecules or more and less than 2.7 molecules of the alkali for each molecule of N-phosphonomethylglycinonitrile. When the alkali cation is divalent, hydrolysis is conducted using alkali so as to result in 1 molecule or more and less than 1.5 molecules of alkali, and preferably 1.05 molecules or more and less than 1.35 molecules of the alkali for each molecule of N-phosphonomethylglycinonitrile.

For each molecule of N-phosphonomethylglycinonitrile, when the added quantity of alkali metal hydroxide results in less than 2 molecules, or the added quantity of alkaline-earth metal hydroxide results in less than 1 molecule, the reaction rate is extremely low and impractical. On the other hand, when the added quantities approach 3 molecules or 1.5 molecules, respectively, the economic efficiencies of reducing the quantity of salt produced as a by-product, which is an object of the present invention, become small. As a result, the quantity of alkali metal hydroxide added, for each molecule of N-phosphonomethylglycinonitrile, results in 2 molecules or more and less than 3 molecules, and preferably 2.1 molecules or more and less than 2.7 molecules. The quantity of alkaline-earth metal hydroxide added for each molecule of N-phosphonomethylglycinonitrile results in 1 molecule or more and less than 1.5 molecules, and preferably 1.05 molecules or more and less than 1.35 molecules.

The reaction can take place in either a closed system or an open system. For an open system, the reaction temperature is in the range of from 60° C. to boiling point, and the reaction time depends on the quantity of alkali and the temperature but is about 5~20 hours. For a closed system, the reaction temperature is 60° C. or greater, and the reaction time depends on the quantity of alkali used and the reaction temperature but is about 0.5~5.0 hours. It is presumed that the reason the reaction time for the closed system is shorter than the reaction time for the open system is because the reaction temperature in the closed system can be raised, and also because the reaction solution is maintained at a high pH since the ammonia produced by the hydrolysis of nitrile cannot escape from the system. Therefore, the reaction time in the closed system can be shortened.

The yield of N-phosphonomethylglycine obtained in this manner is 90% or greater using N-phosphonomethylglycinonitrile as the standard. Depending on the situation, the reaction solution is suitably diluted or concentrated, then the N-phosphonomethylglycine can be isolated easily from this reaction solution by means of acidification. Alternatively, isolation refining can be performed by means of commonly used methods, such as ion exchange resin and the like, either independently or together, and additional refining can be done by means of recrystallization.

In addition, in the present invention, N-phosphonomethylglycine and salts thereof, which are the desired products, can be obtained by hydrolysis of unrefined N-phosphonomethylglycinonitrile by the addition of additional alkali, and the above-mentioned unrefined N-phosphonomethylglycinonitrile is obtained by the reaction of aminomethyl phosphonic acid and glycolonitrile in the presence of alkali, wherein, for each molecule of the above-mentioned aminomethyl phosphonic acid, the number of alkali molecules results in 1.5 molecules or more and less than 2.5 molecules when the alkali is monovalent, and 0.75 molecules or more and less than 1.25 molecules when the alkali is divalent.

When using this method, the total quantity of alkali used for each molecule of N-phosphonomethylglycinonitrile results in 2 molecules or more and less than 3 molecules when the alkali is monovalent, and 1 molecule or more and less than 1.5 molecules when the alkali is divalent.

The alkali salt of N-phosphonomethylglycine which is obtained by means of the alkali hydrolysis of the present invention can be used to obtain the free acid of N-phosphonomethylglycine by conventional means, for example, by using mineral acid. In addition, alkylammonium salts (dimethlyammonium salt, isopropylammonium salt, etc.), alkylsulfonium salts (trimethylsulfonium salt, etc.), and the like can be manufactured by conventional means, for example, the desired salt can be manufactured by means of methods such as U.S. Pat. No. 3,799,758; U.S. Pat. No. 3,977,860; European Patent No. 369,076; and the like.

For example, the isopropylamine salt of N-phosphonomethylglycine can be obtained as a crystalline solid by the agitated reaction, at around room temperature, of N-phosphonomethylglycine and an equivalent molar amount of isopropylamine dissolved in water, followed by heating under reduced pressure, concentration, and drying. The trimethylsulfonium salt of N-phosphonomethylglycine is obtained by using trimethylsulfonium hydroxide in place of isopropylamine.

In a similar way, for example, glyphosate, sodium glyphosate, ammonium glyphosate, glyphosate-monodimethylamine, glyphosphate trimethylsulfonium salt (sulfosate), and glyphosamine can be manufactured.

DESCRIPTION OF THE PREFERRED EMBODIMENTS

In the following, representative examples of the manufacturing method for the N-phosphonomethylglycine of the present invention are given and explained in detail. However, these examples are illustrations for the purpose of giving an understanding of the present invention, the present invention is not limited to only these examples, and it is not possible to limit the present invention based on these examples.

EXAMPLE 1

A 250 ml three-necked round-bottomed flask was equipped with a stirrer, thermometer, and reflux condenser. 150 g of water, 17.5 g of 48% sodium hydroxide aqueous solution (210 mmol), and 15.0 g (100 mmol) of N-phosphonomethylglycinonitrile were added, and heated and refluxed with stirring for 20 hours. The solution was analyzed by means of HPLC and was found to contain 90 mmol of N-phosphonomethylglycine. The reaction yield was 90% with regard to the N-phosphonomethylglycinonitrile starting material. In addition, the pH of this solution was 10.0 (measured by means of a pH meter which was calibrated using a buffer solution of pH 7 at 20° C.; this calibration method was used for all following pH measurements).

After the reaction solution was concentrated to about half its original quantity and neutralized with concentrated hydrochloric acid until it had a pH of 1, it was left overnight and the N-phosphonomethylglycine crystallized. The crystallized N-phosphonomethylglycine was separated by filtration. The quantity, after washing in water and drying, was 13.0 g, with a purity of 98% according to HPLC.

EXAMPLE 2

The reaction was conducted in the same way as in Example 1 with the exception that the quantity of 48% sodium hydroxide was 20 g (240 mmol) and the reaction time was 14 hours. The reaction yield of the solution, according to HPLC analysis, was 95% with regard to the N-phosphonomethylglycinonitrile starting material. In addition, the pH of this solution was 10.4.

EXAMPLE 3

The reaction was conducted in the same way as in Example 1 with the exception that the quantity of 48% sodium hydroxide was 22.5 g (270 mmol) and the reaction time was 12 hours. The reaction yield of the solution, according to HPLC analysis, was 92% with regard to the N-phosphonomethylglycinonitrile starting material. In addition, the pH of this solution was 10.9.

EXAMPLE 4

150 g of water, 17.5 g of 48% sodium hydroxide aqueous solution (210 mmol), and 15.0 g (100 mmol) of N-phosphonomethylglycinonitrile were added to a 300 ml SUS autoclave, and heated and stirred for 2 hours in a closed system at 120° C. in an oil bath. The reaction yield of the solution, according to HPLC analysis, was 88% with regard to the N-phosphonomethylglycinonitrile starting material. In addition, the pH of this solution was 10.7.

EXAMPLE 5

The reaction was conducted in the same way as in Example 4 with the exception that the quantity of 48% sodium hydroxide was 20 g (240 mmol) and the reaction time was 1 hour. The reaction yield of the solution, according to HPLC analysis, was 92% with regard to the N-phosphonomethylglycinonitrile starting material. In addition, the pH of this solution was 11.2.

EXAMPLE 6

The reaction was conducted in the same way as in Example 5 with the exception that 8.9 g of calcium hydroxide (120 mmol) were used in place of 48% sodium hydroxide. The reaction yield of the solution, according to HPLC analysis, was 91% with regard to the N-phosphonomethylglycinonitrile starting material. In addition, the pH of this solution was 11.3.

EXAMPLE 7

A 200 ml four-necked round-bottomed flask was equipped with a stirrer, thermometer, a dropping funnel, and a reflux condenser. A mixed solution of 55 g of water, 18.4 g of 48% sodium hydroxide aqueous solution (220 mmol), and 11.1 g of aminomethyl phosphonic acid (100 mmol) was added and stirred. At this time the pH was 13.1.

The reaction vessel was cooled in iced water and while the reaction solution was being maintained at 5° C. or below, 14.3 g of 40% glycolonitrile solution (100 mmol) was added dropwise for 30 minutes. After the dropwise-addition was completed, the solution was stirred for 30 minutes at 5° C. or below, and then returned to room temperature and stirred for 1 hour. At this time the pH was 11.0.

Next, the solution was heated and refluxed for 20 hours. The solution was analyzed by means of HPLC and was found to contain 91 mmol of N-phosphonomethylglycine. The reaction yield was 91% with regard to the aminomethyl phosphonic acid and glycolonitrile starting materials.

After the reaction solution was neutralized to a pH of 2 using concentrated hydrochloric acid, it was left overnight and the N-phosphonomethylglycine crystallized. The crystallized N-phosphonomethylglycine was separated by filtration. The quantity, after washing in water and drying, was 18.8 g, with a purity of 98% according to HPLC.

EXAMPLE 8

A 200 ml four-necked round-bottomed flask was equipped with a stirrer, thermometer, a dropping funnel, and a reflux condenser. A mixed solution of 50 g of water, 16.7 g of 48% sodium hydroxide aqueous solution (200 mmol), and 11.1 g of aminomethyl phosphonic acid (100 mmol) was added and stirred. At this time the pH was 13.1.

The reaction vessel was cooled in iced water and while the reaction solution was being maintained at 5° C. or below, 14.3 g of 40% glycolonitrile solution (100 mmol) was added dropwise for 30 minutes. After the dropwise-addition was completed, the solution was stirred for 30 minutes at 5° C. or below, and then returned to room temperature and stirred for 1 hour. At this time the pH was 11.0.

Next, 4.2 g of 48% sodium hydroxide solution aqueous solution (50 mmol) was added, and heated and refluxed for 14 hours. The solution was analyzed by means of HPLC and was found to contain 95 mmol of N-phosphonomethylglycine. The reaction yield was 95% with regard to the aminomethyl phosphonic acid and glycolonitrile starting materials.

After the reaction solution was neutralized to a pH of 2 using concentrated hydrochloric acid, it was left overnight and the N-phosphonomethylglycine crystallized. The crystallized N-phosphonomethylglycine was separated by filtration. The quantity, after washing in water and drying, was 19.3 g, with a purity of 98% according to HPLC.

COMPARATIVE EXAMPLE

The reaction was conducted in the same way as in Example 4 with the exception that the quantity of 48% sodium hydroxide was 27.5 g (330 mmol) and the reaction time was 2 hours. The reaction yield of the solution, according to HPLC analysis, was 94% with regard to the N-phosphonomethylglycinonitrile starting material. In addition, the pH of this solution was 12.5.

From the above examples, it is clear that, by means of the manufacturing method of the present invention, N-phosphonomethylglycine and salts thereof can be manufactured by alkali hydrolysis of N-phosphonomethylglycinonitrile, and the amount of salt produced as a by-product when isolating N-phosphonomethylglycine and salts thereof can be reduced.

In addition, it is possible to obtain high yields of high purity N-phosphonomethylglycine and salts thereof.

Industrial Applicability

The N-phosphonomethylglycine and salts thereof manufactured by means of the manufacturing method of the present invention can be biologically degraded, have superior effectiveness against weeds, and are used widely as a herbicide or starting materials for herbicides.

By means of the manufacturing method of the present invention, N-phosphonomethylglycine and salts thereof can be obtained at high yield and high purity, and, moreover, the amount of salt produced as by-product can be reduced.

We claim:

1. A manufacturing method for N-phosphonomethylglycine and salts thereof comprising a step of alkali hydrolysis of N-phosphonomethylglycinonitrile, wherein hydrolysis takes place using an alkali metal hydroxide so as to result in not less than 2 molecules and less than 3 molecules of the alkali metal hydroxide for each molecule of N-phosphonomethylglycinonitrile.

2. A manufacturing method for N-phosphonomethylglycine and salts thereof comprising a step of alkali hydrolysis of N-phosphonomethylglycinonitrile, wherein hydrolysis takes place using alkaline-earth metal hydroxides so as to result in not less than 1 molecule and less than 1.5 molecules of the alkaline-earth metal hydroxides for each molecule of N-phosphonomethylglycinonitrile.

3. A manufacturing method according to claim 1 conducted in a closed system.

4. A manufacturing method according to claim 1, wherein hydrolysis takes place using alkali metal hydroxide so as to result in not less than 2.1 molecules and less than 2.7 molecules of the alkali metal hydroxide for each molecule of N-phosphonomethylglycinonitrile.

5. A manufacturing method according to claim 2, wherein hydrolysis takes place using alkaline-earth metal hydroxides so as to result in not less than 1.05 molecules and less than 1.35 molecules of the alkaline-earth metal hydroxides for each molecule of N-phosphonomethylglycinonitrile.

6. A manufacturing method according to claim 1 for manufacturing N-phosphonomethylglycine and salts thereof comprising:

a first step of reacting aminomethyl phosphonic acid and glycolonitrile in the presence of alkali metal hydroxide so as to result in 1.5–2.5 molecules of the alkali metal hydroxide for each molecule of said aminomethyl phosphonic acid; and a second step in which, without isolating said N-phosphonomethylglycinonitrile obtained in said first step, hydrolysis takes place using sufficient alkali metal hydroxide to neutralize the carboxylic acid generated;

wherein the total amount of alkali metal hydroxide used in said first step and said second step results in not less than 2 molecules and less than 3 molecules for each molecule of said N-phosphonomethylglycinonitrile.

7. A manufacturing method according to claim 3 for manufacturing N-phosphonomethylglycine and salts thereof comprising:

a first step of reacting aminomethyl phosphonic acid and glycolonitrile in the presence of alkali metal hydroxide so as to result in 1.5–2.5 molecules of the alkali metal hydroxide for each molecule of said aminomethyl phosphonic acid; and a second step in which, without isolating said N-phosphonomethylglycinonitrile obtained in said first step, hydrolysis takes place using sufficient alkali metal hydroxide to neutralize the carboxylic acid generated;

wherein the total amount of alkali metal hydroxide used in said first step and said second step results in not less than 2 molecules and less than 3 molecules for each molecule of said N-phosphonomethylglycinonitrile.

8. A manufacturing process according to claim 6 comprising the additional step of manufacturing a trialkylsulfonium salt or an amine salt of N-phosphonomethylglycine by reacting amine or trialkylsulfonium hydroxide with a free acid of N-phosphonomethylglycine obtained by using mineral acid to neutralize an alkali metal salt of said N-phosphonomethylglycine obtained in said second step.

9. A manufacturing method according to claim 2 conducted in a closed system.

10. A manufacturing method according to claim 2 for manufacturing N-phosphonomethylglycine and salts thereof comprising:

a first step of reacting aminomethyl phosphonic acid and glycolonitrile in the presence of alkaline-earth metal hydroxides so as to result in 0.75–1.25 molecules of the alkaline-earth metal hydroxides for each molecule of said aminomethyl phosphonic acid; and a second step in which, without isolating said N-phosphonomethylglycinonitrile obtained in said first step, hydrolysis takes place using sufficient alkaline-earth metal hydroxides to neutralize the carboxylic acid generated;

wherein the total amount of the alkaline-earth metal hydroxides used in said first step and said second step results in not less than 1 molecule and less than 1.5 molecules for each molecule of said N-phosphonomethylglycinonitrile.

* * * * *